United States Patent [19]

Koyama et al.

[11] Patent Number: 5,700,674
[45] Date of Patent: Dec. 23, 1997

[54] MUTANT URICASE, A MUTANT URICASE GENE, A NOVEL RECOMBINANT DNA, AND A PROCESS FOR PRODUCING MUTANT URICASE

[75] Inventors: Yasuji Koyama; Toshio Ichikawa, both of Noda, Japan

[73] Assignee: Kikkoman Corporation, Chiba, Japan

[21] Appl. No.: 701,952

[22] Filed: Aug. 23, 1996

[30] Foreign Application Priority Data

Aug. 24, 1995 [JP] Japan ................................. 7-216239

[51] Int. Cl.⁶ .......................... C12N 9/06; C12N 1/20; C12P 21/06; C07H 21/04
[52] U.S. Cl. .................. 435/191; 435/69.1; 435/252.33; 435/320.1; 536/23.2
[58] Field of Search ......................... 435/191, 69.1, 435/252.33, 320.1; 536/23.2; 530/350

[56] References Cited

U.S. PATENT DOCUMENTS 5,376,545  12/1994  Yagasaki et al. ...................... 435/191

*Primary Examiner*—Rebecca E. Prouty
*Assistant Examiner*—Tekchand Saidha
*Attorney, Agent, or Firm*—Fish & Richardson, P.C.

[57] ABSTRACT

The present invention relates to mutant uricase containing the amino acid sequence of wild-type uricase shown in SEQ ID NO: 1 wherein the 165–170th amino acids contain a mutated amino acid sequence, a mutant uricase gene coding for said uricase, a recombinant DNA having said mutant uricase gene integrated into a vector DNA, and a process for producing mutant uricase by culturing a microorganism carrying said recombinant DNA and having the ability to produce mutant uricase in a medium, and then recovering mutant uricase from the culture. The present invention provides stable mutant uricase and the gene coding for said mutant uricase, and further the process of the present invention enables efficient production of stable uricase.

4 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
    ( A ) LENGTH: 303 amino acids
    ( B ) TYPE: amino acid
    ( C ) STRANDEDNESS: Not Relevant
    ( D ) TOPOLOGY: linear ( i i ) MOLECULE TYPE: protein ( x i ) SEQUENCE DESCRIPTION: SEQ ID NO:1:

```
Met Ser Thr Thr Leu Ser Ser Ser Thr Tyr Gly Lys Asp Asn Val Lys
 1               5                  10                  15

Phe Leu Lys Val Lys Lys Asp Pro Gln Asn Pro Lys Lys Gln Glu Val
                20                  25                  30

Met Glu Ala Thr Val Thr Cys Leu Leu Glu Gly Gly Phe Asp Thr Ser
                35                  40                  45

Tyr Thr Glu Ala Asp Asn Ser Ser Ile Val Pro Thr Asp Thr Val Lys
        50                  55                  60

Asn Thr Ile Leu Val Leu Ala Lys Thr Thr Glu Ile Trp Pro Ile Glu
 65                 70                  75                  80

Arg Phe Ala Ala Lys Leu Ala Thr His Phe Val Glu Lys Tyr Ser His
                85                  90                  95

Val Ser Gly Val Ser Val Lys Ile Val Gln Asp Arg Trp Val Lys Tyr
               100                 105                 110

Ala Val Asp Gly Lys Pro His Asp His Ser Phe Ile His Glu Gly Gly
               115                 120                 125

Glu Lys Arg Ile Thr Asp Leu Tyr Tyr Lys Arg Ser Gly Asp Tyr Lys
       130                 135                 140

Leu Ser Ser Ala Ile Lys Asp Leu Thr Val Leu Lys Ser Thr Gly Ser
145                 150                 155                 160

Met Phe Tyr Gly Tyr Asn Lys Cys Asp Phe Thr Thr Leu Gln Pro Thr
               165                 170                 175

Thr Asp Arg Ile Leu Ser Thr Asp Val Asp Ala Thr Trp Val Trp Asp
               180                 185                 190

Asn Lys Lys Ile Gly Ser Val Tyr Asp Ile Ala Lys Ala Ala Asp Lys
```

```
                         195                    200                          205
        Gly  Ile  Phe  Asp  Asn  Val  Tyr  Asn  Gln  Ala  Arg  Glu  Ile  Thr  Leu  Thr
             210                      215                      220

Thr  Phe  Ala  Leu  Glu  Asn  Ser  Pro  Ser  Val  Gln  Ala  Thr  Met  Phe  Asn
        225                 230                      235                          240

Met  Ala  Thr  Gln  Ile  Leu  Glu  Lys  Ala  Cys  Ser  Val  Tyr  Ser  Val  Ser
                            245                      250                      255

Tyr  Ala  Leu  Pro  Asn  Lys  His  Tyr  Phe  Leu  Ile  Asp  Leu  Lys  Trp  Lys
                       260                      265                      270

Gly  Leu  Glu  Asn  Asp  Asn  Glu  Leu  Phe  Tyr  Pro  Ser  Pro  His  Pro  Asn
                  275                      280                      285

Gly  Leu  Ile  Lys  Cys  Thr  Val  Val  Arg  Lys  Glu  Lys  Thr  Lys  Leu
                  290                 295                      300
```

( 2 ) INFORMATION FOR SEQ ID NO:2:

( i ) SEQUENCE CHARACTERISTICS:
        ( A ) LENGTH: 6 amino acids
        ( B ) TYPE: amino acid
        ( C ) STRANDEDNESS: Not Relevant
        ( D ) TOPOLOGY: linear ( i i ) MOLECULE TYPE: peptide ( x i ) SEQUENCE DESCRIPTION: SEQ ID NO:2:

```
        Phe  Ile  Arg  Asp  Glu  Tyr
        1                   5
```

( 2 ) INFORMATION FOR SEQ ID NO:3:

( i ) SEQUENCE CHARACTERISTICS:
        ( A ) LENGTH: 909 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
ATGTCAACAA  CGCTCTCATC  ATCCACCTAC  GGCAAGGACA  ACGTCAAGTT  CCTCAAGGTC    60
AAGAAGGACC  CGCAAAACCC  AAAGAAGCAG  GAGGTTATGG  AGGCCACCGT  CACGTGTCTG   120
CTTGAAGGTG  GGTTCGACAC  CTCGTACACG  GAGGCTGACA  ACTCGTCCAT  CGTGCCAACA   180
GACACCGTGA  AGAACACCAT  TCTCGTGTTG  GCAAAGACCA  CGGAGATTTG  GCCAATTGAG   240
AGATTTGCAG  CCAAGCTGGC  CACGCACTTT  GTTGAGAAGT  ACTCGCACGT  CTCTGGCGTC   300
TCCGTCAAGA  TTGTCCAGGA  CAGATGGGTC  AAGTACGCCG  TTGATGGCAA  GCCACACGAC   360
CACTCTTTTA  TCCACGAAGG  TGGTGAGAAG  AGAATCACTG  ACCTGTACTA  CAAGAGATCC   420
GGTGATTACA  AGCTGTCGTC  TGCCATCAAG  GACTTGACGG  TGCTGAAGTC  CACCGGCTCG   480
ATGTTCTACG  GCTACAACAA  GTGTGACTTC  ACCACCTTGC  AACCAACAAC  TGACAGAATC   540
TTGTCCACCG  ACGTCGATGC  CACCTGGGTT  TGGATAACA   AGAAGATTGG  CTCTGTCTAC   600
GACATCGCCA  AGGCTGCAGA  CAAGGGAATC  TTTGACAACG  TTTACAACCA  GGCTAGAGAG   660
ATCACCTTGA  CCACCTTTGC  TCTCGAGAAC  TCTCCATCTG  TGCAGGCCAC  GATGTTCAAC   720
ATGGCTACTC  AGATCTTGGA  AAAGGCATGC  TCTGTCTACT  CGGTTTCATA  CGCCTTGCCA   780
AACAAGCACT  ACTTCCTCAT  TGACTTGAAA  TGGAAAGGTT  TGGAGAACGA  CAACGAGTTG   840
TTCTACCCAT  CTCCACATCC  AAATGGGTTG  ATCAAGTGTA  CTGTTGTCCG  TAAGGAGAAG   900
ACCAAGTTG                                                               909
```

( 2 ) INFORMATION FOR SEQ ID NO:4:

( i ) SEQUENCE CHARACTERISTICS:
 ( A ) LENGTH: 48 base pairs
 ( B ) TYPE: nucleic acid
 ( C ) STRANDEDNESS: single
 ( D ) TOPOLOGY: linear ( x i ) SEQUENCE DESCRIPTION: SEQ ID NO:4:

TGGTTGCAAG GTGGTGTATT CATCGCGAAT GAAGCCGTAG AACATCGA    48

MUTANT URICASE, A MUTANT URICASE GENE, A NOVEL RECOMBINANT DNA, AND A PROCESS FOR PRODUCING MUTANT URICASE

1. Field of the Invention

The present invention relates to mutant uricase, a mutant uricase gene, a novel recombinant DNA, and a process for producing mutant uricase.

2. Background of the Invention

Uricase is an enzyme catalyzing the following reaction:

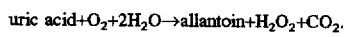

uric acid+$O_2$+2$H_2O$→allantoin+$H_2O_2$+$CO_2$.

Because uric acid in serum or urine can be quantified readily and specifically by quantifying hydrogen peroxide formed by the catalytic action of this enzyme, uricase is extremely useful in the field of clinical diagnosis.

Conventionally, uricase has been produced for example by culturing in a medium a microorganism belonging to the genus Escherichia carrying a recombinant DNA having a *Candida utilis*-derived uricase gene inserted into a vector DNA and then recovering uricase from the culture (Japanese Laid-Open Patent Publication No. 317055/93).

However, the uricase obtained in this prior process is disadvantageous in that when stored as a reagent, it is liable to inactivation owing to lack of oxidative stability and thermostability. It has therefore been desired to develop physically and chemically stable uricase.

SUMMARY OF THE INVENTION

The object of the present invention is to provide physically and chemically stable mutant uricase, a gene coding for said mutant uricase, a recombinant having said gene integrated into it, and a process for producing mutant uricase.

As a result of their eager research, the present inventors found that the above problem can be solved by replacing an amino acid sequence around a specific acid in wild-type uricase by a specific sequence by mutation.

That is, the present invention is a mutant uricase gene coding for a polypeptide containing the amino acid sequence of wild-type uricase shown in SEQ ID NO: 1 wherein the 165–170th amino acids contain a mutated amino acid sequence. An example of such a mutated amino acid sequence is shown in SEQ ID NO: 2.

Further, the present invention is a recombinant DNA having said mutant uricase gene integrated into a vector DNA.

Further, the present invention is a process for producing mutant uricase, which comprises culturing a microorganism belonging to the genus Escherichia carrying said recombinant DNA and having the ability to produce mutant uricase in a medium, and then recovering mutant uricase from the culture.

Further, the present invention is mutant uricase containing the amino acid sequence of wild-type uricase shown in SEQ ID NO: 1 wherein the 165–170th amino acids contain a mutated amino acid sequence. An example of such a mutated amino acid sequence is shown in SEQ ID NO: 2.

The present invention provides stable mutant uricase and the gene coding for said mutant uricase, and further the process of the present invention enables efficient production of stable uricase.

DETAILED DESCRIPTION OF THE INVENTION

The mutant uricase of the present invention has the amino acid sequence of wild-type uricase shown in SEQ ID NO: 1, but with a mutation in the 165–170th amino acids.

Insofar as the desired uricase activity is obtainable, the "mutation" in the present invention is understood as replacement by other amino acids, deletion, or insertion at the 165–170 positions of SEQ ID NO: 1. For example, if the 165th and 166th amino acids are tyrosine and asparagine respectively in wild-type uricase, then the 165th and 166th amino acids in the mutant uricase of the present invention may be replaced respectively by any of 18 kinds of amino acids other than tyrosine and asparagine, or tyrosine and/or asparagine may be deleted, or any amino acid may be inserted between tyrosine and asparagine. This also applies to the 167–170th amino acids.

Now, the mutant uricase gene of the present invention is described.

The mutant uricase gene of the present invention that is a gene coding for said mutant uricase can be obtained by genetic engineering means.

To obtain the mutant uricase of the present invention, it is necessary to prepare a wild-type uricase gene and its recombinant DNA. Any wild-type uricase gene can be used and an example is that derived from a microorganism belonging to the genus Candida.

The wild-type uricase gene etc. are prepared by methods known in the art. For example, a wild-type uricase gene and its recombinant DNA can be prepared through cloning from *Candida utilis* ATCC 9950 as a gene source (see Japanese Laid-Open Patent Publication No. 317055193).

The wild-type uricase is then treated for mutation. This treatment can be carried out in any known method depending on the desired mutation, e.g. by contacting the wild-type uricase gene or a recombinant DNA containing said gene with a chemical agent as mutagen or by ultraviolet radiation, genetic engineering means, protein engineering means etc.

Examples of chemical agents used as mutagen are hydroxylamine, N-methyl-N'-nitro-N-nitrosoguanidine (NTG), nitrous acid, sulfurous acid, hydrazine, formic acid, 5-bromouracil etc.

The conditions for treatment with the mutagen can be selected depending on the type of chemical agent used etc., and are not particularly limited insofar as the desired mutation can actually be induced in the wild-type uricase gene. The desired mutation can generally be induced by treatment with the chemical agent preferably in a concentration of 0.5 to 12M at a reaction temperature of 20° to 80° C. for at least 10 minutes, preferably 10 to 180 minutes. Ultraviolet radiation can also be carried out in a usual manner ("Gendai Kagaku" (Modern Chemistry), pp. 24–30, June issue (1989)).

As protein engineering means, it is possible to use means generally known as site specific mutagenesis. Examples are the Kramer method [Kramer, W. et al., Nucl. Acids Res,12, 9441–9456 (1984); Kramer, W. et al., Methods in Enzymol., 154, 350–367 (1987); Bauer, C. E. et al., Gene, 37, 73–81 (1985)], the Eckstein method [Taylor, J. W. et al., Nucleic Acids Res., 13, 8749–8764 (1985); Taylor, J. W. et al., Nucleic Acids Res. 13, 8765–8785 (1985); Nakamaye K., et al., Nucleic Acids Res. 14, 9679–9698 (1986)]; and the Kunkel method [Kunkel, T. A., Proc. Natl. Acad. Sci. 82, 488–492 (1985); Kunkel, T. A., et al., Methods in Enzymol., 154, 367–382 (1987)].

In addition to the aforementioned gene modification methods, organic synthesis or enzymatic synthesis can also be used to directly synthesize the desired modified uricase gene. The desired uricase gene thus obtained can be determined and confirmed by a method such as the chemical modification method of Maxam and Gilbert [Maxam and Gilbert, Methods in Enzymol., 65, 499–560 (1980)] or the dideoxynucleotide chain termination method using M13 phage [Messing et al., Gene, 19, 269–276 (1982)].

By the aforementioned mutation means, it is possible to obtain the mutant uricase gene coding for a polypeptide containing the amino acid sequence of wild-type uricase wherein the 165–170th amino acids contains a mutated amino acid sequence. An example of such an amino acid sequence where the 165–170th amino acids are mutated is shown in SEQ ID NO: 2. Two or more codons coding for the same amino acid (degenerate codons) may be contained in said gene.

The mutant uricase gene thus obtained can be integrated in a usual manner into a vector such as bacteriophage, cosmid, or plasmid for transformation of procaryotic or eucaryotic cells, to transform or transduce a host compatible with the vector.

Examples of hosts are microorganisms belonging to the genus Escherichia, including E. coli JM101 (ATCC 33876), E. coli DH1 (ATCC 33849), E. coli HB101 (ATCC 33694), and E. coli XL1-blue (purchased from Funakoshi K. K., Japan). If such a microorganism is selected, a transformed or transduced strain can be obtained by transformation according to e.g. the Hanahan method (DNA Cloning, 1, 109–135 (1985)) or transduction according to e.g. the method described in Molecular Cloning, pp. 256–268, Cold Spring Harbor Laboratory (1982).

The resulting strain can be screened for the target transformant i.e. the strain belonging to the genus Escherichia carrying the recombinant DNA having the mutant uricase gene inserted into a vector DNA and having the ability to produce the mutant uricase.

The novel recombinant DNA can be purified from the transformant by a conventional method described in e.g. Current Protocols in Molecular Biology (Wiley Interscience, 1989) unit 1.7.

From the recombinant DNA, the DNA containing the mutant uricase gene can be obtained by treating the plasmid DNA with a restriction enzyme such as EcoRI at 30° to 40° C., preferably around 37° C., for 1 to 24 hours, preferably about 2 hours and then subjecting the reaction solution to agarose gel electrophoresis as described in Molecular Cloning, p. 150, Cold Spring Harbor Laboratory (1982).

Now, the production of the mutant uricase of the present invention is described.

The mutant uricase of the present invention can be obtained by culturing the transformant obtained as described above and purifying uricase from the culture.

Culture may be carried out in a conventional solid medium, but preferably in a liquid medium.

As the medium for culturing said strain, mention may be made of a medium containing one or more nitrogen sources such as yeast extract, trypton, peptone, meat extract, corn steep liquor and exudate of soybean or wheat bran, one or more inorganic salts such as sodium chloride, dipotassium hydrogen phosphate, potassium dihydrogen phosphate, magnesium sulfate, magnesium chloride, ferric chloride, ferric sulfate and manganese sulfate, and if necessary sugars or carbohydrates and vitamins.

The initial pH of medium is adjusted preferably in the range of pH 7–9. Culture is continued for 4 to 24 hours, preferably 6 to 20 hours and at 30° to 42° C., preferably around 37° C., by submerged aeration culture, shake culture, or stationary culture.

After culture is finished, the mutant uricase can be recovered from the culture by conventional enzyme purification means. For example, the enzyme can be extracted by disrupting the microorganisms by ultrasonication or grinding or treatment with lytic enzyme such as lysozyme or released by autolysis of the microorganisms in the presence of a solvent such as toluene optionally under shaking.

Insolubles are removed from the extract by filtration or centrifugation and if necessary nucleic acids are removed by adding streptomycin sulfate, protamine sulfate, manganese sulfate etc. Then, the solution is fractionated with ammonium sulfate, alcohol, acetone etc., and the precipitates are recovered as crude enzyme. This crude enzyme is then purified by chromatography, electrophoresis etc., for example gel filtration on Sephadex, Ultrogel, Biogel etc., adsorption-elution on ion exchanger, electrophoresis on polyacrylamide gel etc., adsorption-elution on hydroxyapatite, sedimentation by sucrose density gradient centrifugation etc., affinity chromatography, and fractionation through molecular sieve membrane, hollow fiber membrane etc. These can be suitably selected or Combined to purify the crude enzyme.

Whether the amino acid sequence of the purified mutant uricase undergoes the desired mutation or not can be confirmed by conventional amino acid analysis, for example the Edman method for automatic amino acid sequencing. The activity of the mutant uricase may be compared with that of wild-type uricase by use of the uricase activity remaining as an index of mutation after heating at 60° C. for 15 minutes.

EXAMPLES

The present invention is illustrated by the following examples which however are not intended to limit the scope of the present invention.

[Example 1]

1. Preparation of recombinant plasmid DNA pUO1001

Recombinant plasmid DNA pUOX101 (deposited as FERM BP-3842) described in Japanese Laid-Open Patent Publication No. 317055/93 was cleaved with restriction enzymes BalI and EcoRI and then separated by agarose gel electrophoresis to give an about 700 bp DNA fragment. This fragment was inserted into pUC119 previously cleaved with HincII and EcoRI to construct recombinant plasmid DNA pUO1001. The nucleotide sequence of the wild-type uricase gene from E. coli JM109 (pUOX101) and its coding amino acid sequence are shown in SEQ ID NOS: 3 and 1, respectively.

2. Acquisition of mutant uricase

Recombinant plasmid DNA pUO1001 was transformed into E. coli CJ236 (purchased from Bio-Rad) and a single-stranded DNA was obtained from recombinant plasmid DNA pUO1001 in usual manner. Site specific mutagenesis was carried out using a Muta-Gene in vitro mutagenesis kit (produced by Bio-Rad) with the single-stranded DNA as a template and the oligonucleotide shown in SEQ ID NO: 4 as a primer.

The mutant DNA thus obtained was transformed into E. coli XL1-Blue (purchased from Funakoshi). Recombinant plasmid DNA pUO1002 was prepared in a usual manner from the transformant.

pUO1002 was cleaved with restriction enzymes BstXI and XhoI and then separated by agarose gel electrophoresis to give a 310 bp DNA fragment. This fragment was inserted into pUOX101 previously cleaved with BstXI and XhoI, and then transformed into E. coli XL1-Blue. The resulting plasmid DNA was designated pUOX101β. The resulting E. coli XL1-Blue (pUOX101 β) has been deposited as FERM BP-5204 with the National Institute of Bioscience and Human-Technology, Agency of Industrial Science and Technology, Japan.

3. Properties of the mutant strain

The *E. coli* XL1-Blue (pUOX101β) thus obtained was incubated at 37° C. for 20 hours in TY medium (1% (W/V) trypton, 0.5% (W/V) yeast extract, 0.5% (W/V) common salt) containing 1 mM IPTG and 100 µg/ml ampicillin, then disrupted by ultrasonication, and centrifuged to give a crude enzyme solution.

0.1 ml of the crude enzyme solution was placed in an Eppendorf tube and heated at 60° C. for 15 minutes. The remaining enzyme activity was determined according to the method described in Agri. Biol. Chem., vol. 31, no. 11, pp. 1256–1264 (1967).

The results are shown in Table 1. For comparison, the value of *E. coli* JM109 (pUOX101) (wild-type), is also shown. In the table, the values in the parentheses indicate the proportion of the enzyme activity remaining after heat treatment to the activity in the untreated crude enzyme solution.

TABLE 1

|  | no treatment | treatment at 60° C., 15 min. |
|---|---|---|
| *E. coli* JM109 (pUOX101) wild-type | 0.738 U/ml (100%) | 0.048 U/ml (6.5%) |
| *E. coli* XL1-Blue (pUOX101β) mutant | 0.807 U/ml (100%) | 0.856 U/ml (106%) |

We claim:

1. An isolated mutant uricase gene coding for a polypeptide containing the amino acid sequence of wild-type uricase shown in SEQ ID NO: 1, wherein the 165–170th amino acids contain a mutated amino acid sequence.

2. The mutant uricase gene according to claim 1, wherein said mutated amino acid sequence is shown in SEQ ID NO: 2.

3. A recombinant DNA having the mutant uricase gene of claim 1 or 2 integrated into a vector DNA.

4. A process for producing mutant uricase, which comprises culturing a microorganism belonging to the genus Escherichia carrying the recombinant DNA of claim 3 and having the ability to produce mutant uricase in a medium, and then recovering mutant uricase from the culture.

* * * * *